(12) United States Patent
Guo et al.

(10) Patent No.: US 11,668,191 B2
(45) Date of Patent: Jun. 6, 2023

(54) DEVICE AND METHOD FOR TESTING THE THREE-PHASE SATURATION OF OIL, GAS AND WATER IN HIGH-TEMPERATURE AND HIGH-PRESSURE PLANAR MODEL

(71) Applicant: SOUTHWEST PETROLEUM UNIVERSITY, Chengdu (CN)

(72) Inventors: Ping Guo, Chengdu (CN); Zhouhua Wang, Chengdu (CN); Yijian Chen, Chengdu (CN); Bowen Sun, Chengdu (CN); Chao Dong, Chengdu (CN); Yisheng Hu, Chengdu (CN); Shuoshi Wang, Chengdu (CN)

(73) Assignee: SOUTHWEST PETROLEUM UNIVERSITY, Chengdu (CN)

( * ) Notice: Subject to any disclaimer, the term of this patent is extended or adjusted under 35 U.S.C. 154(b) by 0 days.

(21) Appl. No.: 17/394,071

(22) Filed: Aug. 4, 2021

(65) Prior Publication Data

US 2022/0290561 A1 Sep. 15, 2022

(30) Foreign Application Priority Data

Mar. 15, 2021 (CN) .......................... 202110304856.8

(51) Int. Cl.
*E21B 49/08* (2006.01)
*E21B 49/00* (2006.01)
(Continued)

(52) U.S. Cl.
CPC .......... *E21B 49/088* (2013.01); *E21B 49/005* (2013.01); *E21B 49/0875* (2020.05);
(Continued)

(58) Field of Classification Search
CPC ..... E21B 49/008; E21B 49/087; E21B 49/088
See application file for complete search history.

(56) References Cited

U.S. PATENT DOCUMENTS

2018/0329112 A1* 11/2018 Lee .................. G01V 99/00

FOREIGN PATENT DOCUMENTS

| CN | 103452541 A | * | 12/2013 | |
|---|---|---|---|---|
| CN | 107121359 B | * | 7/2018 | ............. G01N 11/00 |
| CN | 110500068 A | * | 11/2019 | ............. E21B 43/16 |

* cited by examiner

*Primary Examiner* — John Fitzgerald
(74) *Attorney, Agent, or Firm* — Muncy, Geissler, Olds & Lowe, P.C.

(57) ABSTRACT

A device for testing the three-phase saturation of oil, gas and water in a high-temperature and high-pressure planar model includes a displacement pump, a confining pressure pump, a back pressure pump, containers, a planar model system, a data acquisition system, a back pressure valve and an oil-gas separator. The planar model system includes a planar model, an autoclave body, a heating temperature-controlling system, a Y-axis direction stepping motor, a X-axis direction stepping motor and an acoustoelectric detector. A method for testing the three-phase saturation of oil, gas and water by using the device includes calibrating three-phase saturation of oil, gas and water to a rock core, preparing a formation water sample and a crude sample, regaining the original formation conditions of the planar model, simulating the depletion or displacement process of oil reservoirs, performing linear ultrasonic-and-resistivity-scanning test on planar model, determining the three-phase saturation distribution of oil, gas and water.

9 Claims, 2 Drawing Sheets

(51) Int. Cl.
*G01N 30/02* (2006.01)
*G01N 33/24* (2006.01)
*G01N 33/28* (2006.01)

(52) U.S. Cl.
CPC ........... *G01N 30/02* (2013.01); *G01N 33/241* (2013.01); *G01N 33/2823* (2013.01); *E21B 2200/20* (2020.05); *G01N 2030/025* (2013.01)

DEVICE AND METHOD FOR TESTING THE THREE-PHASE SATURATION OF OIL, GAS AND WATER IN HIGH-TEMPERATURE AND HIGH-PRESSURE PLANAR MODEL

TECHNICAL FIELD OF THE INVENTION

The invention relates to the field of exploration and development of petroleum and natural gas, in particular to an acoustoelectric scanning device and method for testing the three-phase saturation of oil, gas and water in a high-temperature and high-pressure planar model.

DESCRIPTION OF THE PRIOR ART

The well pattern, well type, barrier interference, gravity drive, and development technology policies during developing oil-gas reservoirs are important factors that influence the effect of oil-gas reservoir development. Conventional rock cores (such as a small plunger rock core, a full-diameter rock core, a long rock core) and a low-pressure physical model (such as a glass-etching model) can no longer meet the requirements of real oil-gas reservoir simulation, especially for oil-gas reservoirs that adopt a gas-injecting development method, the displacement effect has to be achieved only under high pressure. Although X-CT and NMR on-line saturation-testing technologies have developed in recent years, the most of tested objects are standard rock cores, but large-scale rock cores cannot be tested.

At present, a saturation-testing device on a large-scale 3D physical model mainly has the following characteristics. First, the most of large-scale 3D physical models are a low-pressure physical model, so the model generally cannot bear pressure more than 25 MPa, and the larger the model, the lower the pressure (Peng Caizhen, Meng Lixin, Guo Ping, et al. *development and application of oil-driving experiment simulation device on 3D physical model [J]. Petroleum Geology & Experiment*, 2013, 35(5): 570-573), in particular, the experimental conditions on a cementing model sintered by high-temperature or an organic-glass-etching model are only normal pressure and temperature, and the crude oil used is a simulated oil, so real formation fluid samples cannot be used (Wu Yunyun. *3D physical simulation experiment of thin interlayer interference [J]. Laboratory Research and Exploration,* 2017, 36(1): 25-29). Second, in the usual saturation-testing experiment on the large-scale 3D physical model, the saturation detector is generally buried in the physical model in the form of a probe, or electrodes are attached to both sides of a rock slab in the form of an array for point-to-point testing, as the saturation probe itself has a certain size, too many probes will have influence on interstitial flow of fluid, and the detector used in the electrode is limited by its own volume, so too many detectors cannot be arranged, resulting in the test accuracy being limited (Yang Jianping. *a device and method for injecting dry gas longitudinal wave into high-temperature and high-pressure condensate gas reservoir and testing efficiency: China,* 104563982[P].2017.02.01). Third, as the existing saturation-testing principle on the large-scale physical model is mostly direct current logging, the probe or electrode must be in direct contact with the rock slab to perform signal acquisition, resulting in reducing the degree of sealing the rock slab, and point-to-point will bring about a large number of signal leads, which have to be led out from the external model under high-temperature and high-pressure conditions, which greatly increases the risk of leakage (Yang Shenglai. *Experimental device for physics simulation to corrode gas reservoirs by water: China,* 206038586[P]. 2017.03.22). Fourth, the existing large-scale physical models generally only execute resistivity-testing and do not have the function of simultaneously testing acoustic wave and electrical resistivity, and they can only simulate water oil-driving or polymer oil-driving process, but cannot simulate the gas-injecting development process of oil-gas reservoirs (e.g. gas oil-driving, gas gas-driving) (Guo Xiao. *3D physical simulation experiment device and saturation-determining method for heterogeneous bottom water reservoirs: China,* 104675394[P]. 2018.01.12). Therefore, designing a high-temperature and high-pressure large-scale 3D physical model and an online test method for three-phase saturation of oil, gas and water to overcome the above shortcomings is of great significance to solve this kind of problems.

SUMMARY OF THE INVENTION

One objective of the invention is to provide a device for testing the three-phase saturation of oil, gas and water in a high-temperature and high-pressure planar model. The device is reliable in the principle, easy to operate, and intuitive in the measurement result, so it is suitable for an acoustoelectric scanning test for three-phase saturation of oil, gas and water in the high-temperature and high-pressure 3D physical model, and provides tools and means for research on testing three-phase saturation of oil, gas and water, monitoring at pre-displacement, deploying different injection-production well patterns, heterogeneity in reservoirs, gravity drive and displacement mechanism of various well types during the depletion and displacement development of oil-gas reservoirs.

Another objective of the invention is to provide a method for testing the three-phase saturation of oil, gas and water in a high-temperature and high-pressure planar model by using the above device. It provides guiding opinions for quantitatively determining the three-phase saturation of oil, gas and water during the depletion and displacement development of oil-gas reservoirs, and has broad application prospects.

In order to achieve the above technical objectives, the invention adopts the following technical solutions.

A device for testing the three-phase saturation of oil, gas and water in a high-temperature and high-pressure planar model is mainly composed of a displacement pump, a confining pressure pump, a back pressure pump, a formation water intermediate container, a crude intermediate container, a dry gas intermediate container, a high-temperature and high-pressure planar model system, an acoustoelectric test positioning control and data acquisition system, a back pressure valve, an oil-gas separator, a gas meter and an oil-gas chromatograph.

The high-temperature and high-pressure planar model system is mainly composed of a planar model, a high-temperature and high-pressure autoclave body, an autoclave body frame, a fastening system, a heating temperature-controlling system, a Y-axis direction stepping motor, an X-axis direction stepping motor, a Y-axis direction sliding rail, an X-axis direction sliding rail, a Y-axis direction sliding bock, an X-axis direction sliding block, an acoustoelectric detector and an autoclave body cover plate. The planar model is fixed on the inner end surface of the autoclave body cover plate, and embedded in the high-temperature and high-pressure autoclave body. The autoclave body cover plate is equipped with a wire passer, an autoclave body inlet, a confining-pressure-fluid-injecting inlet, an autoclave body outlet, and the autoclave body cover plate and the high-temperature and high-pressure autoclave body are fastened with each other by the fastening system and hung on the autoclave body frame as a entire. Both sides of the planar model are equipped with the Y-axis direction stepping motor, the X-axis direction stepping motor, the Y-axis direction sliding rail, the X-axis direction sliding rail, the Y-axis direction sliding bock and the X-axis direction sliding block. The Y-axis direction stepping motor is fixed at one end of the X-axis direction sliding block and is integrated with the Y-axis direction sliding rail, and integrally installed on the X-axis direction sliding rail. The acoustoelectric detector is fixed on the Y-axis direction sliding block, driven by the Y-axis direction stepping motor to linearly slide along the Y-axis direction sliding rail, performing the acoustoelectric scanning test. The X-axis direction stepping motor drives the X-axis direction sliding block to linearly slide along the X-axis direction sliding rail. During the entire testing process, the acoustoelectric detector moves along the X/Y direction and moves in a zigzag pattern, so that the acoustoelectric detector completes the acoustoelectric scanning test to the entire planar model. The planar model is fastened by fastening bolts. There is an injection inlet on the left side of the model and a collecting outlet on the right side. The autoclave body inlet is connected with the injection inlet on the planar model by a pipeline, and the autoclave body outlet is connected with the collecting outlet on the planar model by a pipeline. The hydraulic oil enters the annular space between the high-temperature and high-pressure autoclave body and the planar model through the confining-pressure-fluid-injecting inlet. Both sides of the planar model are equipped with the heating temperature-controlling systems to detect and control temperature, so as to realize heating the oil bath inside the high-temperature and high-pressure autoclave body. All electric wires and signal wires inside the autoclave body are led out by the wire passer.

The displacement pump is respectively connected to the high-temperature and high-pressure autoclave body inlet through the formation water intermediate container, the crude intermediate container, and the dry gas intermediate container. The confining pressure pump is connected to the confining-pressure-fluid-injecting inlet, and the internal electric wires and signal wires are connected to the acoustoelectric test positioning control and data acquisition system by the wire passer. The autoclave body outlet is sequentially connected to the oil-gas separator, the gas meter, and the oil-gas chromatograph through the back pressure valve, and the top of the back pressure valve is connected to the back pressure pump.

The heating temperature-controlling system, the pressure sensor, the acoustoelectric detector, and the stepping motor system are all connected to the acoustoelectric test positioning control and data acquisition system to realize collecting temperature data, pressure data, ultrasonic data, resistivity data, and controlling the movement of the stepping motor.

The planar model is mainly composed of a model cover plate, a sand-filling model, and a planar pressure-bearing cavity. A layer of rubber sheath is laid between the model cover plate and the sand-filling model, and fastened by fastening bolts to fully seal them up.

The acoustoelectric detector is mainly composed of an acoustoelectric transmission probe and an acoustoelectric reception probe. There are 1 ultrasonic-transmitting chip and 1 induction-transmitting coil inside the acoustoelectric transmission probe, and there are 1 ultrasonic-receiving chip and 1 induction-receiving coil inside the acoustoelectric reception probe. According to the principle of ultrasound, when the acoustoelectric transmission probe generates ultrasonic waves (longitudinal waves), the ultrasonic waves pass through the planar model to reach the acoustoelectric reception probe. The oscilloscope obtains the position of the head wave, after processing data, the interval transit time at the current location of the acoustoelectric detector can be obtained. According to the principle of induction logging, when the induction-transmitting coil in the acoustoelectric transmission probe is energized with alternating current, an alternating magnetic field is formed around the coil, and an induced current (eddy current) is generated in the rock slab. The secondary magnetic field caused by the eddy current causes a secondary induced current in the induction-receiving coil, after processing data, the resistivity at the current location of the acoustoelectric detector can be obtained. The acoustic wave signal wire and the resistance signal wire are separated from each other and do not interfere with each other.

The high-temperature high-pressure autoclave body realizes 0~180° rotation by an autoclave body rotating mechanism. The autoclave body rotating mechanism is mainly composed of a motor, a two-stage reducer and a rotating shaft. The motor revolves forward and backward by adjusting the frequency converter to achieve adjusting the inclination angle of the autoclave body and simulating the gravity drive of oil-gas reservoirs at different inclination angles.

The key components used in the invention are described as follows.

(1) Planar model: the planar pressure-bearing cavity used in the experiment has maximum displacement pressure of 70 MPa, maximum confining pressure of 80 MPa, and maximum working temperature of 150° C., has the working cavity volume with length (1000 mm), width (300 mm) and depth (10 mm), and the material is high-carbon steel, and the inner and outer surfaces are treated with rust prevention. It includes a model bottom plate, a model cover plate, an overlying rubber sheath, fastening bolts, etc.

(2) High-temperature high-pressure autoclave body: this sealed model is a cylindrical autoclave body with flange diameter of 900 mm, length of 1750 mm, and height of 2.3 m, adopts a columnar double-stage sealing and flange connection, and the autoclave body is rotated by a motor through a two-stage reducer and can stay at any position.

(3) Autoclave body frame: it is shaped with length of 2000 mm, width of 1500 mm, and height of 1600 mm by welding rectangular steel pipes, equipped with two 6" directional wheels and two 6" universal wheels having brakes for easy movement and installation.

(4) Autoclave body rotating mechanism: it is mainly composed of a frequency converter, a motor, a two-stage reducer, and a rotating shaft. The motor revolves forward and backward by adjusting the frequency converter to achieve adjusting the inclination angle of the device.

(5) Fastening system: it is composed of M64 external hexagonal fastening bolts with mechanical strength more than 8.8, used for installing and fastening the autoclave body and the flange.

(6) Heating temperature-controlling system: both the bottom plate and the cover plate of the planar model are equipped with heating pipes with power of 3.5 Kw×4 and AC 380V power supply, and the temperature-controlling system is used to detect and control temperature.

(7) Confining pressure system: an electric turbocharged pump is used to inject hydraulic oil into the autoclave body to raise the pressure, the pressure range is 0~90 MPa, and the accuracy is 0.1 MPa.

(8) Stepping motor system: the stepping motor can realize speed adjustment at 0.01-1000 mm/min, with step error of <+0.1%, maximum operating temperature of 150° C. and no requirement of sealed environment, withstand high pressure, have oil-resistance, and realize mechanical zeroing.

(9) Acoustoelectric detector: the acoustoelectric detector includes an acoustoelectric transmission probe and an acoustoelectric reception probe. There are 1 ultrasonic-transmitting chip and 1 induction-transmitting coil inside the acoustoelectric transmission probe, and there are 1 ultrasonic-receiving chip and 1 induction-receiving coil inside the acoustoelectric reception probe. The acoustic wave signal wire and the resistance signal wire are separated from each other, with good insulation. The ultrasonic test and the resistivity test can be performed simultaneously, with no requirement of sealed environment for the probe, high-temperature resistance, high-pressure resistance, and oil-resistance, and the maximum working temperature is 150° C.

(10) Pressure sensor: the pressure sensors are installed the injection inlet on the planar model, the collecting outlet, the confining-pressure-fluid-injecting inlet, and at the top of the back pressure valve, with a working range of 0~100 MPa.

(11) Acoustoelectric test positioning control and data acquisition system: it mainly collects temperature data, pressure data, ultrasonic data, and resistivity data.

A method for testing the three-phase saturation of oil, gas and water in a high-temperature and high-pressure planar model by using the above device sequentially includes the following steps:

S1. Calibrating Three-Phase Saturation of Oil, Gas and Water to a Representative Core so as to Obtain Calibration Formulas.

Saturating the representative core with formation water by using a set of small core holders, and measuring the core resistivity $R_o$ at this time, and then continuously injecting the separator oil sample into the core to measure the rock resistivity $R_t$ at different water saturations $S_w$, obtaining Archie Formula $$\frac{R_t}{R_o} = \frac{b}{S_w^n}$$

suitable to calculating the water saturation of the planar sand filling model by data regression; fully saturating the core with formation water again, displacing the core to the bound water state with dry gas, continuing to raise the core pressure to the original formation pressure with dry gas pressure, and then continuously injecting the separator oil sample into the core to measure the interval transit time of cores ΔT at different gas saturation $S_g$, obtaining the relational expression $S_g=a\cdot\Delta T+b$ between the gas saturation $S_g$ and the interval transit time of cores by data regression; finally, after obtaining the water saturation $S_w$ and the gas saturation $S_g$ by the above calibration method, calculating the oil saturation $S_o=1-S_w-S_g$.

S2. Preparing Formation Fluid Samples

Obtaining the separator gas sample and the separator oil sample under the oilfield site production conditions, preparing crude oil samples at original formation temperature and pressure, and ensuring that the gas-oil ratio and the bubble point pressure are close to those in the PVT report of the crude oil in this stratum, and then preparing a formation water sample according to the formation water analysis report provided by the oilfield site.

S3. Saturating the Planar Model with Formation Fluid and Regaining the Original Formation Conditions Adjusting the high-temperature and high-pressure autoclave body to the angle required for the experiment, increasing the back pressure to the original formation pressure, injecting the formation water sample into the planar model and fully saturating it, and then pressurizing the planar model with the formation water to increase its hole pressure to the original formation pressure, during the pressure-forming process, keeping the confining pressure always higher than the hole pressure of the planar model by 5 MPa, and raising the internal temperature of the high-temperature and high-pressure autoclave body to the original formation temperature and keeping it stable; then not injecting the crude oil sample into the planar model to replace the formation water until the formation water in the oil-gas separator no longer increases, and building up the original formation conditions of the planar model.

S4. Simulating the Depletion or Displacement Process of Oil Reservoirs, Performing Linear Ultrasonic-and-Resistivity-Scanning Test on Planar Model.

If equipped with a single acoustoelectric detector, during testing, the acoustoelectric detector sliding and scanning in a zigzag pattern along the X/Y direction until completing the acoustoelectric scanning operation on the entire planar model, this process being capable of simultaneously testing the interval transit time and the resistivity at the position of the acoustoelectric detector. If equipped with side-by-side acoustoelectric detectors, during testing, the acoustoelectric detector linearly sliding in the X direction until completing the acoustoelectric scanning operation on the entire planar model, this process being capable of simultaneously testing the interval transit time and the resistivity at the position of the acoustoelectric detector.

If it is necessary to test the three-phase saturation of oil, gas and water during the depletion development of oil reservoirs, deleting the hole pressure of the planar model to the bubble point pressure, and after the hole pressure being stable, continuing to decreasing the pressure until the hole pressure of the planar model down to the waste pressure, testing the interval transit time and the resistivity of the entire planar model by the acoustoelectric detector under various pressures, and feeding back the information to the data acquisition system, meanwhile, collecting the separator gas in the gas meter and the separator oil in the oil-gas separator under various pressures during the depletion process, and taking oil-gas chromatographic analysis by the oil-gas chromatograph.

If it is necessary to test the three-phase saturation of oil, gas and water during the gas injection development of oil reservoirs, quantitatively injecting the dry gas sample into the planar model, and after the hole pressure of the planar model being stable, testing the interval transit time and the resistivity of the entire planar model by the acoustoelectric detector, and feeding back the information to the data acquisition system, meanwhile, collecting the separator gas in the gas meter and the separator oil in the oil-gas separator under various pressures during the depletion process, and taking oil-gas chromatographic analysis by the oil-gas chromatograph.

(5) processing data, quantitatively determining the three-phase saturation distribution of oil, gas and water in the planar model.

According to the calibration formula $$\frac{R_t}{R_o} = \frac{b}{S_w^n}$$

of the water saturation $S_w$ and the measured rock resistivity $R_t$, the calibration formula $Sg = a \cdot \Delta T + b$ of the gas saturation $S_g$ and the interval transit time $\Delta T$, the calibration formula $S_o = 1 - S_w - S_g$ of the oil saturation that are established in S1, substituting the interval transit time and the resistivity data collected during the experiment into the above formula, that being capable of quantitatively determining the three-phase saturation distribution of oil, gas and water at each position of the planar model under the corresponding conditions.

The invention is reliable in the principle, easy to operate, with strong applicability, has a sliding scanning test performed on the flat planar model by combining the acoustoelectric detector and the stepping motor system to greatly reducing the number of acoustoelectric detectors, and both the acoustoelectric detector and the planar model embedded in the high-temperature and high-pressure autoclave body to solve the sealing problem under high-temperature and high-pressure conditions, and provides a new high-resolution, high-temperature and high-pressure large-scale 3D physical model and on-line test method for the three-phase saturation of oil, gas and water, for research on testing three-phase saturation of oil, gas and water, monitoring at pre-displacement, deploying different injection-production well patterns, heterogeneity in reservoirs, gravity drive and displacement mechanism of various well types during the depletion and displacement development of oil-gas reservoirs.

Compared with the prior art, the invention has the following advantages and beneficial effects:

(1) The developed planar model has maximum displacement pressure of 70 MPa, maximum confining pressure of 80 MPa, and maximum working temperature of 150° C., and the model volume is 1000 mm×300 mm×10 mm. It can be rotated from 0~180° to realize the research on the gravity drive of oil-gas reservoirs in dip angle.

(2) The acoustoelectric detector has a built-in ultrasonic chip and induction coil, can simultaneously takes an ultrasonic and resistivity test, with powerful function, while most of the existing saturation detectors are a resistance detector and do not have the ultrasonic testing function.

(3) The method using a stepping motor system to drive the acoustoelectric detector to perform a sliding scanning test on the planar model greatly reduces the number of required detectors and leads. In accordance with the test accuracy, multiple or side-by-side acoustoelectric detectors can be assembled to reduce test time.

(4) The acoustoelectric detector has a built-in transmitting coil and receiving coil, using the test method of induction logging, the detector can measure the resistivity of the rock slab not needing direct contact with it, so the sealing performance of the model is greatly improved. The traditional saturation-testing method is a direct current test method, which requires burying a probe in the model or attaching an electrode to both sides of the rock slab, so it is likely to cause leakage of the model.

In the figures: 1—displacement pump, 2—confining pressure pump, 3—back pressure pump, 4,5,6,7,8,9,10,11,12, 13—valve, 14—formation water intermediate container, 15—crude intermediate container, 16—dry gas intermediate container, 17,18,19,20—pressure sensor, 21—high-temperature and high-pressure planar model system, 22—acoustoelectric test positioning control and data acquisition system, 23—back pressure valve, 24—oil-gas separator, 25—gas meter, 26—oil-gas chromatograph, 27—planar model, 28—injection inlet on the planar model, 29—collecting outlet on the planar model, 30—fastening bolt, 31—high-temperature and high-pressure autoclave body, 32—autoclave body frame, 33—fastening bolt, 34—heating temperature-controlling system, 35—Y-axis direction stepping motor, 36—X-axis direction stepping motor, 37—Y-axis direction sliding rail, 38—X-axis direction sliding rail, 39—Y-axis direction sliding bock, 40—X-axis direction sliding block, 41—acoustoelectric detector, 42—autoclave body cover plate, 43—wire passer, 44—autoclave body inlet, 45—confining-pressure-fluid-injecting inlet, 46—autoclave body outlet, 47—planar model cover plate, 48—sand-filling model, 49—planar pressure-bearing cavity, 50—acoustoelectric transmission probe, 51—acoustoelectric reception probe, 52—autoclave body rotating mechanism.

DETAILED DESCRIPTION OF THE INVENTION

The invention will be further described below based on the drawings and examples to help to understand it for a person skilled in the art. However, it should be clear that the invention is not limited to the scope of the specific embodiments. For a person killed in the art, as long as changes are define by the appended claims and within the scope of the spirit and scope of the invention, they are all claimed by the invention.

Figure 1:
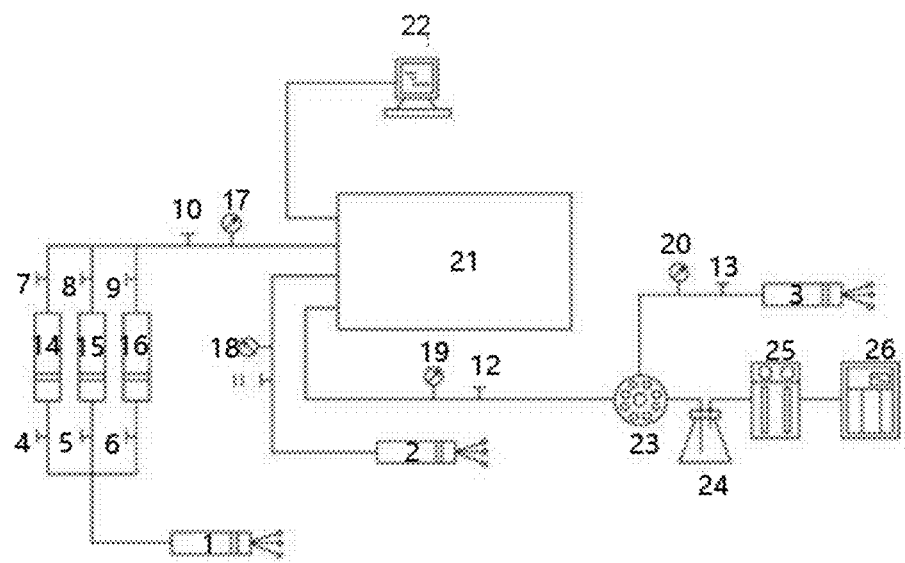
FIG. 1 is a structure diagram of a device for testing the three-phase saturation of oil, gas and water in a high-temperature and high-pressure planar model.
Figure 2:
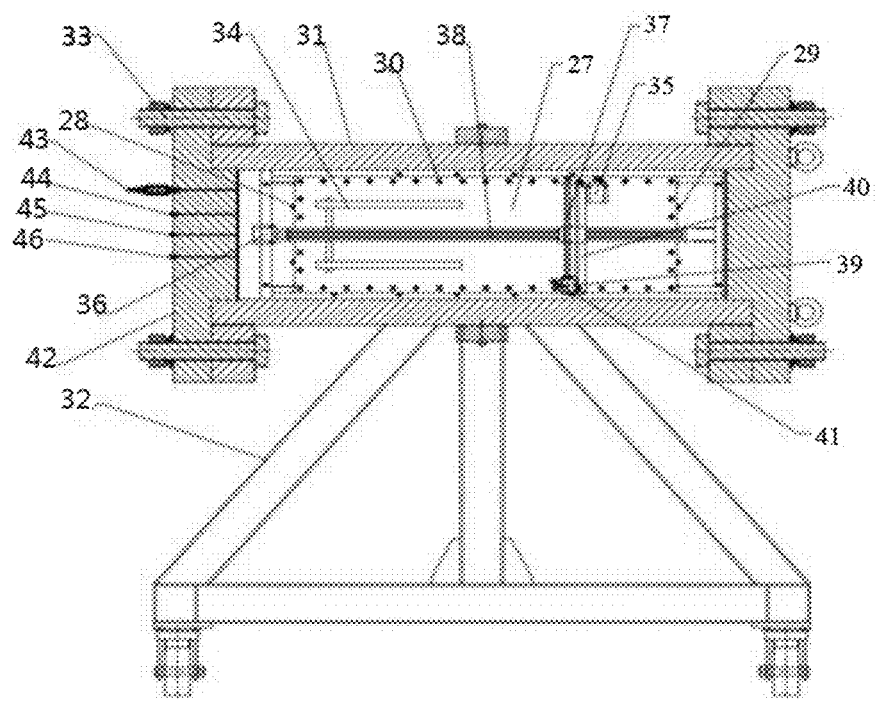
FIG. 2, FIG. 3 and FIG. 4 are the front view, top view, and left view of the high-temperature and high-pressure planar model system, respectively.
Figure 3:
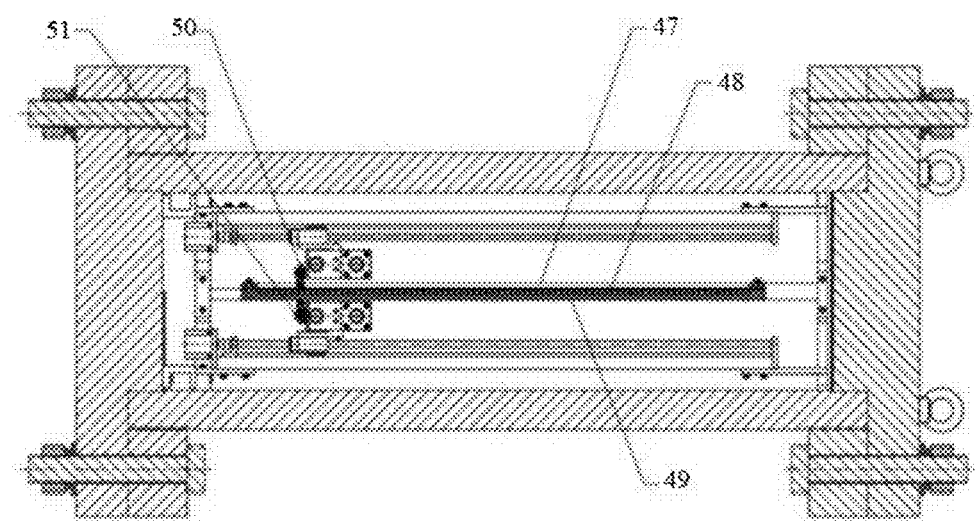
Figure 4:
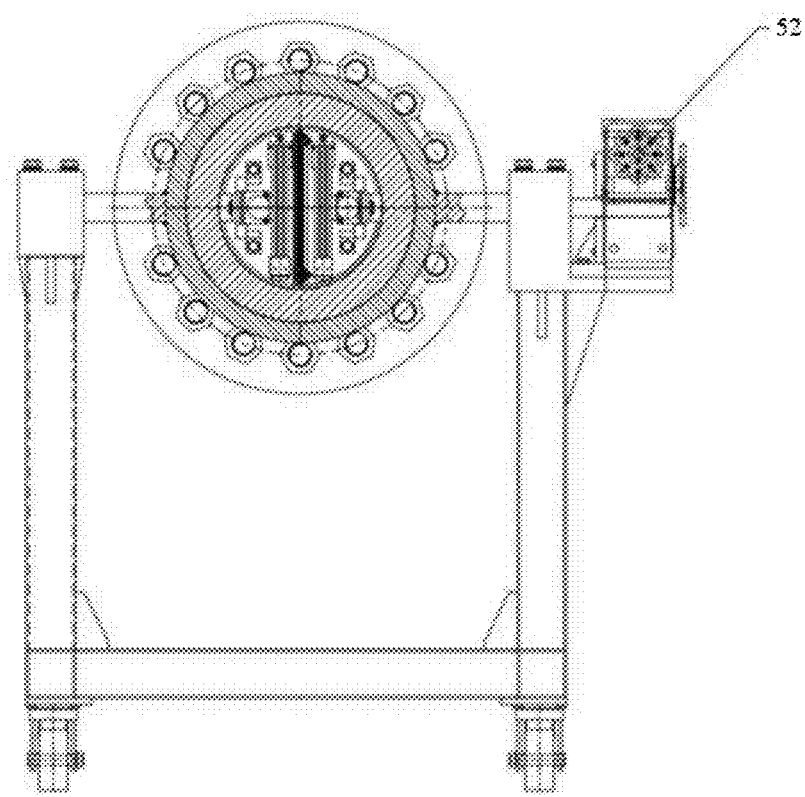

Refer to FIG. 1, FIG. 2, FIG. 3, and FIG. 4.

A device for testing the three-phase saturation of oil, gas and water in a high-temperature and high-pressure planar model includes a displacement pump 1, a confining pressure pump 2, a back pressure pump 3, a formation water intermediate container 14, a crude intermediate container 15, a dry gas intermediate container 16, a high-temperature and high-pressure planar model system 21, an acoustoelectric test positioning control and data acquisition system 22, a back pressure valve 23, an oil-gas separator 24, a gas meter 25 and an oil-gas chromatograph 26.

The high-temperature and high-pressure planar model system 21 includes a planar model 27, a high-temperature and high-pressure autoclave body 31, an autoclave body frame 32, a heating temperature-controlling system 34, a Y-axis direction stepping motor 35, an X-axis direction stepping motor 36, a Y-axis direction sliding rail 37, an X-axis direction sliding rail 38, a Y-axis direction sliding bock 39, an X-axis direction sliding block 40, an acoustoelectric detector 41 and an autoclave body cover plate 42. The high-temperature and high-pressure autoclave body 31 is placed on the autoclave body frame 32, having two autoclave body cover plates 42 on both its sides (the high-temperature and high-pressure autoclave body and the autoclave body cover plate 42 are fastened by fastening bolts 33). An autoclave body inlet 44, a confining-pressure-fluid-injecting inlet 45, and an autoclave body outlet 46 are provided on the autoclave body cover plate 42. The planar model 27 is embedded in the high-temperature and high-pressure autoclave body and fixed on the inside of the autoclave body cover plate, and has an injection inlet 28 on its left side and a collecting outlet 29 on its right side. The autoclave body inlet 44 is connected to the injection inlet 28 on the planar model through a pipeline, and the autoclave body outlet 46 is connected to the collecting outlet 29 on the planar mode by a pipeline. The confining-pressure-fluid-injecting inlet 45 is connected to the annular space between the high-temperature and high-pressure autoclave body and the planar model. The hydraulic oil enters the annular space through the confining-pressure-fluid-injecting inlet. The planar model is equipped with the heating temperature-controlling system 34 to detect and control temperature, so as to realize heating the oil bath inside the high-temperature and high-pressure autoclave body.

The planar model includes a model cover plate 47, a sand-filling model 48, and a planar pressure-bearing cavity 49. Both sides of the planar model are equipped with the Y-axis direction stepping motor 35, the X-axis direction stepping motor 36, the Y-axis direction sliding rail 37, the X-axis direction sliding rail 38, the Y-axis direction sliding bock 39 and the X-axis direction sliding block 40. The Y-axis direction stepping motor is fixed at one end of the X-axis direction sliding block and is integrated with the Y-axis direction sliding rail, and integrally installed on the X-axis direction sliding rail. The acoustoelectric detector 41 is fixed on the Y-axis direction sliding block, driven by the Y-axis direction stepping motor to linearly slide along the Y-axis direction sliding rail, performing the acoustoelectric scanning test. The X-axis direction stepping motor drives the X-axis direction sliding block to linearly slide along the X-axis direction sliding rail.

The displacement pump 1 is respectively connected to the high-temperature and high-pressure autoclave body inlet 44 through the formation water intermediate container 14, the crude intermediate container 15, and the dry gas intermediate container 16. The confining pressure pump 2 is connected to the confining-pressure-fluid-injecting inlet 45, and the autoclave body outlet 46 is sequentially connected to the oil-gas separator 24, the gas meter 25, and the oil-gas chromatograph 26 through the back pressure valve 23, and the top of the back pressure valve 23 is connected to the back pressure pump 3. Pressure sensors (17, 18, 19, 20) are arranged at the autoclave body inlet, the confining-pressure-fluid-injecting inlet, the autoclave body outlet, and the back pressure valve, respectively. The heating temperature-controlling system, the pressure sensor, the acoustoelectric detector, the Y-axis direction stepping motor and the X-axis direction stepping motor are all connected to the acoustoelectric test positioning control and data acquisition system 22 to realize colleting temperature, pressure, ultrasonic waves, and resistivity data and controlling the movement of the stepping motor.

The planar model includes a model cover plate 47, a sand-filling model 48, and a planar pressure-bearing cavity 49. A rubber sheath is arranged between the model cover plate and the sand-filling model, and fastened by a fastening bolt 30 to fully seal them up. The sand-filling model is located inside the planar pressure-bearing cavity.

There is a wire passer 43 on the autoclave body cover plate, and all the electric wires and signal wires inside the autoclave body are connected to the acoustoelectric test positioning control and data acquisition system via the wire passer 43.

The acoustoelectric detector includes an acoustoelectric transmission probe 50 and an acoustoelectric reception probe 51.

During the testing process, the acoustoelectric detector moves along the X/Y direction and moves in a zigzag pattern, so that the acoustoelectric detector completes the acoustoelectric scanning test to the entire planar model.

The high-temperature and high-pressure autoclave body realizes 0~180° rotation through an autoclave body rotating mechanism 52.

A method for testing the three-phase saturation of oil, gas and water in a high-temperature and high-pressure planar model by using the above device includes the following steps:

(1) Processing a Planar Model

Processing the flat model 27 that includes the planar model cover plate 47 and the planar pressure-bearing cavity 49, customizing a hole on the end face of the planar pressure-bearing cavity 49 according to the actual well position, and drilling the injection inlet 28 on the planar model and the collecting outlet 29 on the planar model. Designing well-spacing pipelines according to different well types and well trajectories, such as vertical wells, inclined wells, horizontal wells, etc., the well-spacing pipelines passing through the holes and being buried in the grooves of the planar pressure-bearing cavity 49. According to the actual position of an interlayer (the interlayer refers to the rock layer that is consecutive or inconsecutive in the lateral direction showing low permeability or impermeability in the reservoir profile) in reservoirs, being capable of filling mudstone or placing impermeable rubber strips at the corresponding position of the grooves of the planar pressure-bearing cavity 49 to serve as an interlayer.

(2) Making the Sand-Filling Model and Finishing Assembling the Model

Determining the plan to fill sands based on the core data provided by the oilfield site, mixing cement and quartz sand with water in a certain proportion, stirring the mixture to make the three parts evenly fused, drilling out a small plunger core to test its physical parameters such as permeability and permeability after the sample is dried, if the physical parameters meet the experimental requirements, selecting the above mix to make the sand-filling model 48. Pouring the prepared sand-filled sample into the groove of the planar pressure-bearing cavity 49 to make it evenly filled, cementing it under external force, and solidifying it after drying. Covering the surface of the sand-filling model 48 with a rubber sheath, covering the planar model cover plate 47, and fixing and sealing with the fastening bolt 30. Fixing the fabricated planar model 27 on the inside end surface of the autoclave body cover plate 42, installing the Y-axis direction stepping motor 35, the X-axis direction stepping motor 36, the Y-axis direction sliding rail 37, the X-axis direction sliding rail 38, the Y-axis direction sliding bock 39 and the X-axis direction sliding block 40 on both sides of the planar model 27, fixing the acoustoelectric detector 41 on the Y-axis direction sliding block 39, installing the heating temperature-controlling system 34 on both sides of the planar model 27 to detect and control temperature. Connecting the autoclave body inlet 44 with the injection inlet 28 on the planar model by a pipeline, meanwhile connecting the autoclave body outlet 46 with the collecting outlet 29 on the planar model by a pipeline, leading out ultrasonic signal wires, resistance signal wires, stepping motor control wires and heating wires from the wire passer 43. Hoisting the planar plate model 27 to a position flush with the high-temperature and high-pressure autoclave body 31 by using a lifting device, and slowly pushing it in, fastening the high-temperature and high-pressure autoclave body 31 with autoclave body the cover plate 42 by the fastening system 33. Connecting all experimental devices according to FIG. 1 and closing all valves, connecting the displacement pump 1 to the high-temperature and high-pressure autoclave body inlet 44 through the formation water intermediate container 14, the crude intermediate container 15, and the dry gas intermediate container 16, respectively, and connecting the confining pressure pump 2 to the confining-pressure-fluid-injecting inlet 45, connecting the internal wires of the autoclave body led out by the wire passer 43 to the acoustoelectric test positioning control and data acquisition system 22, connecting the autoclave body outlet 46 to the oil-gas separator 24, the gas meter 25, and the oil-gas chromatograph 26 through the back pressure valve 23 in turn, connecting the top of the back pressure valve 23 to the back pressure pump 3.

(3) Calibrating Three-Phase Saturation of Oil, Gas and Water to a Representative Core As the high-temperature and high-pressure large-scale 3D physical model system 21 requires a large amount of assembly work each time, in order to ensure the success rate of the experiment, the representative small plunger core drilled out in step 2 will be used for the calibration of three-phase saturation oil, gas and water being separately carried out in a small core holder. First, calibrating the relationship between the water saturation $S_w$ and the measured rock resistivity $R_t$, fully saturating the core with formation water, and measuring the core resistivity $R_o$ at this time, then injecting a separator oil sample into the core at a gradient of 0.1 PV (PV, core hole volume), and measuring the rock resistivity $R_t$ under different water saturations $S_w$, performing experimental data regression on $S_w$ and the corresponding experimental data $$\frac{R_t}{R_o}$$

in the double logarithmic coordinate system to determine the parameters b and n of Archie Formula $$(\frac{R_t}{R_o} = \frac{b}{S_w^n})$$

applicable to the planar sand-filling model, or obtaining the parameters b and n through empirical coefficients (such as b=1, n=2 generally for sandstone). Second, calibrating the relationship between the air saturation $S_g$ and the interval transit time $\Delta T$, fully saturating the core with formation water, displacing the core to the bound water state with dry gas, continuing to raise the core pressure to the original formation pressure $P_1$ with dry gas pressure, and then injecting the separator oil sample into the core at a gradient of 0.1 PV to measure the interval transit time of cores $\Delta T$ at different gas saturation $S_g$, performing experimental data regression fitting on $S_g$ and the corresponding the interval transit time $\Delta T$ in a rectangular coordinate system to obtain the relational expression $S_g = a \cdot \Delta T + b$ between the gas saturation $S_g$ and the interval transit time of cores. Third, after obtaining the water saturation $S_w$ and the gas saturation $S_g$ by the above calibration method, calculating the oil saturation $S_o = 1 - S_w - S_g$.

(4) Preparing Formation Fluid Samples

Obtaining the separator gas sample and the separator oil sample under the oilfield site production conditions, preparing crude oil samples at original formation temperature T and pressure $P_1$ according to GB/T 26981-2011, and ensuring that the gas-oil ratio and the bubble point pressure are close to those in the PVT report of the crude oil in this stratum, and then preparing a formation water sample according to the formation water analysis report provided by the oilfield site. Putting the prepared crude sample into the crude intermediate container 15, the formation water sample into the formation water intermediate container 14, and the separator gas sample into the dry gas intermediate container 16.

(5) Saturating the Planar Model With Formation Fluid and Regaining the Original Formation Conditions Placing the confining-pressure-fluid-injecting inlet 45 at vertical upward position through the autoclave body rotating mechanism 52, opening the valve 11, and injecting hydraulic oil into the high-temperature and high-pressure autoclave body 31 in a constant-speed mode by using the confining pressure pump 2, when the hydraulic oil overflows from the drain valve of the autoclave body emptying valve, stopping filling and closing the drain valve. Adjusting the high-temperature and high-pressure autoclave body 31 to the angle required for the experiment by the autoclave body rotating mechanism 52, opening the valve 13, and increasing the back pressure of the back pressure valve 23 to the original formation pressure $P_1$ in a constant-pressure mode by using the back pressure pump 3, opening the valves 4, 7, 10, and 12, injecting the formation water sample from the formation water intermediate container 14 into the planar model 27 in a constant-speed mode by the displacement pump 1 and making it fully saturated, after completion, increasing the hole pressure of the planar model 27 to the original formation pressure P1 by continuing to raise the pressure with the formation water by the displacement pump 1 in a constant-pressure mode, during the pressure-forming process, keeping the confining pressure of the high-temperature and high-pressure autoclave body 31 always higher than the hole pressure of the planar model by 5 MPa by using the confining pressure pump 2, closing the valves 4 and 7, raising the internal temperature of the high-temperature and high-pressure autoclave body 31 to the original formation temperature T by the heating temperature-controlling system 34 and keeping it stable. Opening the valves 5 and 8, injecting the crude sample of the crude intermediate container 15 into the planar model 27 through the displacement pump 1 in a constant-speed mode so as to replace the formation water, not closing the valves 5, 8 and 10 until the formation water in the oil-gas separator 24 no longer increases, and building up the original formation conditions of the planar model 27.

(6) Simulating the Depletion or Displacement Process of Oil Reservoirs, Performing Linear Ultrasonic-and-Resistivity-Scanning Test on Planar Model.

Setting the stepping motor speed and the single-stepping distance by the acoustoelectric test positioning control and data acquisition system 22, wherein the motor speed will directly influence the scanning speed of the acoustoelectric detector 41, the single-stepping distance can be determined according to the required test accuracy, that is, the smaller the single-stepping distance, the denser the sampling points of the acoustoelectric detector, and the more accurate the saturation test result, but the experiment time and cost will increase with it. If the Y-axis direction sliding block 39 is only equipped with a single acoustoelectric detector, controlling the Y-axis direction stepping motor 35 to drive the acoustoelectric detector to move linearly along the Y-axis direction sliding rail 37, and the X-axis direction stepping motor 36 to drive the acoustoelectric detector to move linearly along the X-axis direction sliding rail 38 by the acoustoelectric test positioning control and data acquisition system 22, during testing, the acoustoelectric detector sliding and scanning in a zigzag pattern along the X/Y direction until completing the acoustoelectric scanning operation on the entire planar model, this process being capable of simultaneously testing the interval transit time and the resistivity at the position of the acoustoelectric detector. If the Y-axis direction sliding block 39 is equipped with a row of acoustoelectric detectors, controlling the X-axis direction stepping motor 36 to drive a row of acoustoelectric detectors to move linearly along the X-axis direction sliding rail 38, during testing, the acoustoelectric detector linearly sliding in the X direction until completing the acoustoelectric scanning operation on the entire planar model.

If it is necessary to test the three-phase saturation of oil, gas and water during the depletion development of oil reservoirs, firstly deleting the hole pressure of the planar model 27 to the bubble point pressure $P_2$ by the back pressure pump 3 in a constant-pressure mode, and after the hole pressure being stable, continuing to decreasing the pressure until the hole pressure of the planar model down to the waste pressure $P_3$, testing the interval transit time and the resistivity of the planar model 27 by the acoustoelectric detector 41 under various pressures according to the above introduction, and feeding back the information to the data acquisition system 22, meanwhile, collecting the separator gas in the gas meter 25 and the separator oil in the oil-gas separator 24 under various pressures during the depletion process, and taking oil-gas chromatographic analysis by the oil-gas chromatograph 26.

If it is necessary to test the three-phase saturation of oil, gas and water during the gas injection development of oil reservoirs, opening valves 6, 9, and 10, and not injecting the separator gas sample of the dry gas intermediate container 16 into the planar model 27 at a gradient of 0.1 PV in a constant-speed mode through the displacement pump 1 until 2.0 PV (totally 20 times), every time injecting 0.1 PV of separator gas and after the hole pressure of the planar model being stable, testing the interval transit time and the resistivity of the entire planar model 27 by the acoustoelectric detector 41 according to the above introduction, and feeding back the information to the data acquisition system 22, meanwhile, collecting the separator gas in the gas meter 25 and the separator oil in the oil-gas separator 24 under various pressures during the depletion process, and taking oil-gas chromatographic analysis by the oil-gas chromatograph 26.

(7) Processing Data, Quantitatively Determining the Three-Phase Saturation Distribution of Oil, Gas And Water in the Planar Model.

According to the calibration formula $$\frac{R_t}{R_o} = \frac{b}{S_w^n}$$

of the water saturation $S_w$ and the measured rock resistivity $R_t$, the calibration formula $Sg=a\cdot\Delta T+b$ of the gas saturation $S_g$ and the interval transit time $\Delta T$, the calibration formula $S_o=1-S_w-S_g$ of the oil saturation that are established in step 3, substituting the interval transit time and the resistivity data obtained by the data acquisition system 22 into the above formula, that being capable of quantitatively determining the three-phase saturation distribution of oil, gas and water at each position of the planar model under the corresponding conditions.

The invention claimed is:

1. A device for testing the three-phase saturation of oil, gas and water in a high-temperature and high-pressure planar model includes a displacement pump, a confining pressure pump, a back pressure pump, a formation water intermediate container, a crude intermediate container, a dry gas intermediate container, a high-temperature and high-pressure planar model system, an acoustoelectric test positioning control and data acquisition system, a back pressure valve, an oil-gas separator, a gas meter and an oil-gas chromatograph, wherein said high-temperature and high-pressure planar model system includes a planar model, a high-temperature and high-pressure autoclave body, an autoclave body frame, a heating temperature-controlling system, a Y-axis direction stepping motor, a X-axis direction stepping motor, a Y-axis direction sliding rail, a X-axis direction sliding rail, a Y-axis direction sliding bock, a X-axis direction sliding block, an acoustoelectric detector and an autoclave body cover plate; said high-temperature and high-pressure autoclave body is placed on the autoclave body frame, having two autoclave body cover plates on both its sides, an autoclave body inlet, a confining-pressure-fluid-injecting inlet, and an autoclave body outlet are provided on the autoclave body cover plate, said planar model is embedded in the high-temperature and high-pressure autoclave body and fixed on the inside of the autoclave body cover plate, and has an injection inlet on its left side and a collecting outlet on its right side, the autoclave body inlet is connected to the injection inlet on the planar model and the autoclave body outlet 46 is connected to the collecting outlet on the planar mode by a pipeline, the confining-pressure-fluid-injecting inlet 45 is connected to the annular space between the high-temperature and high-pressure autoclave body and the planar model, said planar model is equipped with the heating temperature-controlling system, said planar model includes a model cover plate, a sand-filling model, and a planar pressure-bearing cavity, both sides of the planar model are equipped with the Y-axis direction stepping motor, the X-axis direction stepping motor, the Y-axis direction sliding rail, the X-axis direction sliding rail, the Y-axis direction sliding bock and the X-axis direction sliding block, said Y-axis direction stepping motor is fixed at one end of the X-axis direction sliding block and is integrated with the Y-axis direction sliding rail, and integrally installed on the X-axis direction sliding rail, said acoustoelectric detector is fixed on the Y-axis direction sliding block, driven by the Y-axis direction stepping motor to linearly slide along the Y-axis direction sliding rail, the X-axis direction stepping motor drives the X-axis direction sliding block to linearly slide along the X-axis direction sliding rail; said displacement pump is respectively connected to the high-temperature and high-pressure autoclave body inlet through the formation water intermediate container, the crude intermediate container, and the dry gas intermediate container, the confining pressure pump is connected to the confining-pressure-fluid-injecting inlet, and the autoclave body outlet is sequentially connected to the oil-gas separator, the gas meter, and the oil-gas chromatograph through the back pressure valve, and the top of the back pressure valve is connected to the back pressure pump, pressure sensors are arranged at said autoclave body inlet, said confining-pressure-fluid-injecting inlet, said autoclave body outlet and said the back pressure valve, respectively, said heating temperature-controlling system, said pressure sensor, said acoustoelectric detector, said Y-axis direction stepping motor and said X-axis direction stepping motor are all connected to the acoustoelectric test positioning control and data acquisition system to realize collecting temperature, pressure, ultrasonic waves, and resistivity data and controlling the movement of the stepping motor.

2. The device for testing the three-phase saturation of oil, gas and water in a high-temperature and high-pressure planar model according to claim 1, wherein a rubber sheath is arranged between the model cover plate and the sand-filling model, and fastened by a fastening bolt to fully seal them up, the sand-filling model is located inside the planar pressure-bearing cavity.

3. The device for testing the three-phase saturation of oil, gas and water in a high-temperature and high-pressure planar model according to claim 1, wherein a wire passer is provided on the autoclave body cover plate, and all the electric wires and signal wires inside the autoclave body are connected to the acoustoelectric test positioning control and data acquisition system via the wire passer.

4. The device for testing the three-phase saturation of oil, gas and water in a high-temperature and high-pressure planar model according to claim 1, wherein said acoustoelectric detector includes an acoustoelectric transmission probe and an acoustoelectric reception probe.

5. The device for testing the three-phase saturation of oil, gas and water in a high-temperature and high-pressure planar model according to claim 1, wherein during the test process, said acoustoelectric detector moves along the X/Y direction and moves in a zigzag pattern, so that the acoustoelectric detector completes the acoustoelectric scanning test to the entire planar model.

6. The device for testing the three-phase saturation of oil, gas and water in a high-temperature and high-pressure planar model according to claim 1, wherein said high-temperature and high-pressure autoclave body realizes 0-180° rotation through an autoclave body rotating mechanism.

7. A method for testing the three-phase saturation of oil, gas and water in a high-temperature and high-pressure planar model by using the device according to claim 1, comprising the following steps:
S1. calibrating three-phase saturation of oil, gas and water to a rock core so as to obtain calibration formulas;
S2. preparing crude oil samples at original formation temperature and pressure, preparing a formation water sample according to the formation water analysis report provided by the oilfield site;
S3. regaining the original formation conditions of the planar model;
S4. simulating the depletion or displacement process of oil reservoirs, performing linear ultrasonic-and-resistivity-scanning test on planar model;
S5. substituting the interval transit time and the resistivity data that are collected, into the formula of S1, determining the three-phase saturation distribution of oil, gas and water.

8. The method according to claim 7, wherein in S4, the process for testing the three-phase saturation of oil, gas and water during the depletion development of oil reservoirs includes: deleting the hole pressure of the planar model to the bubble point pressure, and after the hole pressure being stable, continuing to decreasing the pressure until the hole pressure of the planar model down to the waste pressure, testing the interval transit time and the resistivity of the entire planar model by the acoustic-electric detector under various pressures, and feeding back the information to the data acquisition system, meanwhile taking oil-gas chromatographic analysis by the oil-gas chromatograph.

9. The method according to claim 7, wherein in S4, the process for testing the three-phase saturation of oil, gas and water during the gas injection development of oil reservoirs includes: quantitatively injecting the dry gas sample into the planar model, and after the hole pressure of the planar model being stable, testing the interval transit time and the resistivity of the entire planar model by the acoustic-electric detector, and feeding back the information to the data acquisition system, meanwhile taking oil-gas chromatographic analysis by the oil-gas chromatograph.

* * * * *